United States Patent [19]

Vary et al.

[11] Patent Number: 4,735,897
[45] Date of Patent: Apr. 5, 1988

[54] METHOD AND KIT FOR DETECTING POLYRIBOADENOSINE SEGMENTS AND MESSENGER RNA

[75] Inventors: Calvin P. H. Vary, Califon; Steven E. Diamond, Springfield, both of N.J.; Neil M. Wolfman, Brookline; Astrid P. Koudelka, West Somerville, both of Mass.

[73] Assignees: Allied Corporation, Morristown, N.J.; Genetics Institute, Inc., Cambridge, Mass.

[21] Appl. No.: 729,502

[22] Filed: May 2, 1985

[51] Int. Cl.$^4$ .......................... C12Q 1/68; C12Q 1/50; C12Q 1/42; G01N 33/53

[52] U.S. Cl. ............................................ 435/6; 435/7; 435/17; 435/21; 435/810; 436/501; 536/26; 536/27; 536/28; 935/77; 935/82

[58] Field of Search ...................... 435/6, 7, 91, 17, 21, 435/810; 935/77, 78, 82; 436/501, 808; 536/26, 27, 28

[56] References Cited

U.S. PATENT DOCUMENTS 4,446,231 5/1984 Self .......................................... 435/7

FOREIGN PATENT DOCUMENTS 0063879 11/1982 European Pat. Off. .
8403520 9/1984 PCT Int'l Appl. .

OTHER PUBLICATIONS

Molloy, G. R. et al., Biochem, 11 No. 17:3256–3260 (1972).
Soreq, H. et al., Journ Molec. Biol. 88:233–245 (1974).
Holm–Hansen, O., et al., Methods in Enzymology, vol. LVII: pp. 73–85, (1978).
Dunn, A. R., et al., Methods in Enzymology, vol. 65, pp. 468–478 (1980).
Littauer et al., "Polynucleotide Phosphorylase" in *The Enzymes*, vol. XV (1982), pp. 517–553.

*Primary Examiner*—Robert J. Warden
*Assistant Examiner*—Jack Spiegel
*Attorney, Agent, or Firm*—Alan M. Doernberg

[57] ABSTRACT

RNA such as messenger RNA is digested to nucleotide phosphates including AMP or ADP. The ATP or a byproduct of the phosphorylation, e.g., pyruvate, is detected. Exemplary enzymes used (with appropriate co-reactants and co-factors) are: (1) polynucleotide phosphorylase, pyruvate kinase and luciferase, or (2) phosphodiesterase (or RNase), myokinase, pyruvate kinase and luciferase. The phosphorylation to ATP (e.g., with pyruvate kinase) is preferably coupled with the previous (reversible) enzymatic step.

25 Claims, No Drawings

METHOD AND KIT FOR DETECTING POLYRIBOADENOSINE SEGMENTS AND MESSENGER RNA

The present invention relates to methods and kits for detecting nucleic acids, and especially for detecting polyriboadenosine segments such as those found in eukaryotic messenger RNA.

Ribonucleic acids (RNA) are detected in biological samples by a variety of optical and chromatographic techniques. Such techniques do not easily distinguish total messenger RNA (mRNA) from other forms of RNA such as ribosomal RNA (rRNA), transfer RNA (tRNA) and viral RNA. Tests based upon hybridization detect only specific sequences and not total messenger RNA.

Messenger RNA from eukaryotic cells is known to contain 3'-terminal polyriboadenosine segments of varying lengths which, in some cases, decrease an average length over the lifetime of the mRNA. Such poly A tails have been removed for research purposes by the reaction of polyribonucleotide phosphorylases (PNP) (enzyme registry number 2.7.7.8) in the presence of inorganic phosphate. Such reactions were for purposes of removing the poly A tail without digesting the message part of the mRNA, whose local internal base pairing or "structure" cuts off PNP degradation. See, U. Z. Littauer et al., "Polynucleotide Phosphorylase", in The Enzymes, vol. XV, pp. 517–553, especially 535–537 and 548–553 (Acad. Press 1982).

Various clinical chemistry assays employ ADP and/or adenosine triphosphate (ATP) as either a reagent or as the analyte. Representative assays for ATP as analyte include those described in F. R. Leach, Journal of Applied Biochemistry, vol. 3, pp. 473–517 (1981). Representative assays in which ADP and/or ATP are present in an amount functionally related to the selected analyte include those described in U.S. Pat. No. 4,446,231 to Self. Again, mRNA is not disclosed in these references as a selected analyte.

The ultimate detection in such assays for or via ATP is generally by a light-generating ATP-dependent enzymatic reaction (e.g., the luciferase-catalyzed luciferin reaction with ATP) or by an oxidation or reduction dependent upon an ADP byproduct (e.g., the conversion of NAD to NADH or of NADH to NAD which is dependent upon pyruvate and catalyzed by lactate dehydrogenase).

BRIEF DESCRIPTION OF THE INVENTION

No assay is believed to be known which combines the digestion of a 3'-terminal polyriboadenosine segment with a phosphorylation to ATP. Additionally, the beneficial effects of coupling these steps (by having the ADP phosphorylated as it is produced by digestion) have not been appreciated by the prior art.

Accordingly, the present invention provides a method for the determination of polynucleotides having 3'-terminal polyriboadenosine segments in a sample which comprises the steps:

(a) digesting the nucleic acid of the sample with a polynucleotide phosphorylase in the presence of inorganic phosphate to convert 3'-terminal polyriboadenosine segments to ADP;

(b) phosphorylating the ADP produced in the digesting step (a) to produce ATP; and (c) detecting the ATP produced in the phosphorylating step (b) or a byproduct of the phosphorylating step.

The present invention also provides a kit for the determination of polynucleotides having 3'-terminal polyriboadenosine segments which comprises:

(a) a polynucleotide phosphorylase;

(b) a kinase and its organophosphate coreactant, and (c) reactants for the detection of ATP or of the byproduct formed from the organophosphate coreactant.

The present invention also provides a similar method and kit wherein single-stranded RNA is digested with a phosphodiesterase to nucleoside monophosphates including AMP and the AMP is first phosphorylated to ADP by reaction with myokinase and with a nucleoside triphosphate other than ATP. The ADP is then phosphorylated to ATP and detected as in the other forms of the invention.

DETAILED DESCRIPTION OF THE INVENTION

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3', 5'-phosphodiester linkages, and linked by carbon-nitrogen bonds at the 1-carbon of the sugar to pendant purine or pyrimidine bases such as, but not limited to uracil (linked naturally to ribose only as rU), thymine (linked naturally to deoxyribose only as dT), cytosine (in dC or rC), adenine (in dA or rA) and guanine (in dG or rG). Polynucleotides thus include strands of deoxyribonucleic acid (DNA) and strands of ribonucleic acid (RNA) or continuous heteropolymers of both types of polynucleotides.

The ends of such Polynucleotide Strands are referred to as the Five Prime (5') ends, where the 5-carbon of the pentose is not linked to another pentose (but may bear hydroxyl, monophosphate or other natural or synthetic moieties), or the Three Prime (3') ends, where the 3-carbon of the pentose is not linked to another pentose (but may similarly bear hydroxyl, monophosphate or other natural or synthetic moieties).

If the method of the present invention is to be used for analyzing endogeneous RNA, the sample should be prepared to separate target RNA from cell wall materials, associated proteins or other extraneous materials by one or more of sonication, filtration, centrifugation or extraction under conditions or in combinations known for isolating cellular RNA such as mRNA.

The method of the present invention includes, in some forms, converting certain RNA segments in a sample to nucleoside diphosphates including especially ADP, and converting the ADP to ATP. The ATP is generally then detected. In certain forms of the invention, the coproduct (e.g., pyruvate) is detected. For the ATP detected to be a function of the RNA segments degraded, the background values due to endogenous ADP and endogenous ATP should be treated, preferably in one or more of three techniques: (1) separating endogenous ADP and ATP (and in some cases AMP) from the sample before digestion, (2) converting the endogenous ADP and ATP (and in some cases AMP) to a by-product not producing signal (e.g., AMP or adenosine) before digestion, or (3) determining a background value of ATP due to endogenous ADP and endogenous ATP (and in some cases AMP) and then subtracting such background value. The first two techniques are described now with respect to sample preparation. The third technique is described below after the discussion of ATP detection.

To remove endogenous ADP and endogenous ATP (and in some cases endogenous AMP) from a sample to be analyzed (e.g., a cell extract containing unknown amounts of mRNA), various known physiochemical means may be used. They include extraction, chromatography and precipitation.

To convert endogenous ADP and endogenous ATP (and in some cases endogenous AMP) to a non-signal-producing byproduct various biochemical means may be used. Such biochemical means include treatment with phosphatase enzymes such as bacterial alkaline phosphatases or calf phosphatase or tobacco acid phosphatase. Such phosphatases may be provided on a column or other solid phase. In any event, the phosphatase should be removed or inactivated before the subsequent digestion step. Alternatively, chromatographic techniques may be used.

The sample, optionally after such endogenous ADP and ATP removal, is now ready for digestion with polynucleotide phosphorylase (PNP). Such enzyme (also called polyribonucleotide phosphorylase) can be obtained from a number of sources such as *E. coli* or from *Micrococcus leuteus*. See *The Enzymes*, vol. XV, Part B, pp. 518–556 (Academic Press; P. D. Boyer, ed., 1983); see also U.S. Pat. 4,331,762 to Nakajima et al. (1982).

Conditions for the digesting step are, in general, chosen for efficient enzymatic activity in the desired direction (many of the enzymes used are capable of catalyzing the reverse reaction whereby ribonucleotides are added to the 3' end of the polyribonucleotide segment). For polynucleotide phosphorylase, this reaction can be illustrated as follows:

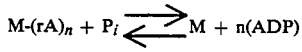

The term M in the above formulae indicates the "message" part of mRNA (all of the mRNA polynucleotide chain except for the poly A tail). PNP proceeds processively from the 3' end, stopping generally at points of double-strandedness (for mRNA, internal base-pairing or sites of ribosomal binding). Provided that the salt conditions are approximately 0.1–0.4 M and temperature is moderate (below about 25° C.), short internal base-pairing segments will remain intact. While some additional nucleotides at the 3' end of the message portion may be cleaved, PNP is likely to reach a double stranded segment soon after leaving the poly A tail. Under these conditions, many other RNAs (ribosomal RNA, transfer RNA, viral RNA) are likely to have limited single-stranded segments at the 3' end, and will therefore produce relatively few nucleoside diphosphates only some (generally 20–30%) of which will be ADP.

If the conditions at the time of digestion are less conducive to internal pairing (e.g., 50° C. or higher) and/or low salt (0.05 M or lower), then somewhat more of the mRNA will be digested before the PNP reaches a stable double-stranded region, and some of the other RNAs will be digested. Nuclear RNA might be expected to denature at these conditions which are less conducive to internal pairing; however, these RNA's contain only part riboadenosine (rather than the poly A tails of mRNA). Transfer RNA (tRNA) has internal pairing segments only 4–5 base pairs long, but has compact structure and methylated sugar residues which stop PNP digestion. In some cases, therefore, only limited additional digestable RNA segments will produce ribonucleoside disphosphates, and only some of the additional nucleosides diphosphates produced are ADP and will therefore lead to a signal.

In addition to sample RNAs, either reagent RNAs or reagent 3'-terminal RNA segments may be digested in the first step of the method of the present invention. Such reagent RNAs and reagent hybrids of DNA with a 3'-terminal terminal RNA segment are described in an application of C. Vary et al., U.S.S.N. 729,503, filed May 2, 1985, the relevant disclosure of which is incorporated herein by reference. As indicated there, the amount of such reagent RNA or reagent DNA-RNA present at the time of digestion will be functionally dependent upon a sequence-specific hybridization event, and especially a strand displacement event. Thus the reagent polyonucleotide (RNA or RNA-DNA) can be a probe with a target binding region substantially complementary to a target nucleotide sequence (a sequence to be determined) and a 3'-terminal (polyriboadenosine segment). It can also be a signal strand displaced from a probe strand by target nucleotide sequence in a sample.

An important preferred feature of the present invention is the coupling of PNP digestion with phosphorylation, and preferably in situ phosphorylation, of the ADP produced by digestion to ATP.

Conversion of ADP to ATP usually involves a kinase (such as pyruvic acid kinase or PK) and an organphosphate reagent (e.g., phosphoenolpyruvic acid). The reaction catalyzed by this reaction is irreversible:

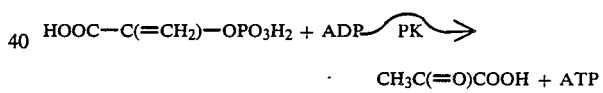

Enzymes that will similarly convert ADP to ATP (in the presence of appropriate organophosphate reagents) include: creatine phosphokinase (CPK in the presence of excess creatine phosphate). See U.S. Pat. No. 4,286,057 to Wulff et al. Exemplary references for such enzymes, showing appropriate reaction conditions, include W. D. McElroy and M. A. DeLuca, *J. Appl. Biochem.*, vol. 5, pp. 197–209 (1983).

In some preferred forms of the present invention, the enzymes and reactants for the digesting step and for the phosphorylating step are present together; either because of being introduced as a single stored reagent or by being introduced as separate reagents so as to contact the displaced labeled polynucleotide together. Using polynucleotide phosphorylase (PNP), creatine phosphokinase (CPK) and creatine phosphate (CP) as exemplary, the overall reaction scheme can be:

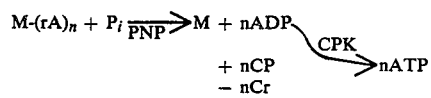

wherein inorganic phosphate and creatine phosphate (CP) are provided in excess. So long as creatine (Cr)

does not build up to an unacceptable degree, the CPK-catalyzed second step will be essentially irreversible, driving the first step in the forward direction as well. Normal cofactors and conditions for the analogous PK reaction include Tris-HCl (pH 8.5), 2-mercaptoethanol 1 mM, of pyruvate kinase (PK) (0.4 units/ml), 0.1 M phosphate and phosphoenol pyruvate (PEP) (4.1 mg/ml).

In some forms of the invention, it is contemplated to digest RNA to nucleoside monophosphates with a phosphodiesterase such as snake venom phosphodiesterase or a ribonuclease, such as a ribonuclease specific for single-stranded ribonucleotide segments. The AMP produced can be converted to ADP by the myokinase-catalyzed reaction:

$$AMP + NTP \rightleftharpoons ADP + NDP$$

where NTP is a nucleoside triphosphate other than ATP (e.g., GTP, CTP, TTP, dGTP, dCTP, dATP, dXTP or dUTP). Because this reaction is reversible, it is preferably coupled with a reaction converting ADP to ATP (e.g., the pyruvate kinase/phosphoenol pyruvate reaction).

Once ATP is produced by the above steps in an amount functionally related to the amount of adenosine phosphate digested from mRNA or an RNA or DNA-RNA reagent, the ATP may be detected in a number of ways, many of which are conventional for the detection of ATP. Exemplary is the luciferin/luciferase method described in various references including U.S. Pat. Nos. 3,933,592 to Clendenning and 3,423,290 to Seamans (Chappelle) (1969) and the above-cited chapter of The Enzymes, vol. XV. The detection of the emitted light generally is conducted in a luminometer or other light-detector such as an LKB Wallac Company Model 1250 luminometer.

Preferred reagents and conditions for the bioluminscent ATP-detecting step include those described in LKB's U.S. Pat. Nos. 4,235,961 to Lundin (1980) and 4,246,340 to Lundin et al. (1981). In the Examples, below, an LKB instrument and LKB reagents were used after the completion of the digestion and phosphorylation steps (carried out together). As indicated in the above LKB patents, the bioluminescent reaction can be controlled (especially with D-luciferin analogs and pyrophosphate) to produce a level signal over one minute while a reading is being taken. Because it is frequently desired that such one minute follow initiation of the bioluminescent reaction by a specified interval, it is preferred that one or both of luciferase and luciferin not be introduced into the reaction mixture until such known interval before detection (e.g., introduced separately into the luminometer instrument).

Numerous other schemes for detecting ATP (with AMP as the byproduct) are known. They include several cited or discussed in U.S. Pat. No. 4,446,231 to Self (1984), the relevant disclosure of which is incorporated by reference. The byproduct of such reactions is AMP, in an amount corresponding on a molar bases both to the ATP consumed and to the photons emitted.

If further amplification is desired, an enzyme such as myokinase may be present (during the detecting step) which catalyzes the reaction:

$$ATP + AMP \rightleftharpoons 2 ADP$$

To complete the recycle, however, it would be necessary that the phosphorylating enzyme and its organo-phosphate reagent (e.g., CPK and CP) also be present during the readout and that conditions suitable for all steps of the recycle be maintained in the luminometer chamber. Furthermore, the various enzymes and reagents introduced must be free of undesired contaminents (e.g., AMP, ADP or ATP) and undesired activities (e.g., catalyzing the hydrolysis of ATP, ADP or of the organophosphate).

Still other ATP-detecting schemes do not produce AMP as the byproduct. They include reactions which release ADP as the byproduct such as the NAD-linked reactions using 3-phophoglycerol kinase and glyceroaldehyde-3-phosphate dehydrogenase.

The ADP produced in the digestion step (d) may also be detected by reaction with phosphoenol pyruvate in the presence of pyruvate kinase, lactate dehydrogenase (LDH) and either NADH or NADPH. In such case, the first reaction is again:

$$PEP + ADP \rightarrow pyruvate + ATP$$

Now, however, instead of (or in addition to) detecting the ATP, the following LDH-catalyzed reaction can occur:

$$NADH + pyruvate \rightarrow NAD + lactate$$

By monitoring the rate of disappearance of NADH (by absorbance at 340 nm), a value can be obtained functionally related to the ADP produced in the digestion step. Other means for detecting the pyruvate (e.g., reaction with DNP-hydrazine) may be used. Furthermore, by having present reactants and enzymes which consume ATP (e.g., fructose-6-phosphate (F6P) and phosphofructose kinase (PFK)), each ADP produced by the digestion step can be recycled as follows:

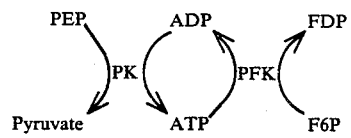

The above is analogous to col. 8 of U.S. Pat. No. 4,446,231 to Self. The above amplification scheme can be accelerated if the pyruvate kinase used is one activated by fructose-1,6-diphosphate (FDP) such as E. coli pyruvate kinase type I. It should be emphasized that, in such schemes, the ADP is provided (by the digestion step) in limited amounts and the pyruvate is being detected (by LDH-catalyzed oxidation of NADH or otherwise).

Other direct or indirect assays for the AMP or ADP produced directly by the digestion step, or for the ATP produced directly or indirectly from such AMP or ADP are described or can be ascertained from the following U.S. Pat. Nos.:

4,331,762 to Nakajuma et al. (1982)
4,338,395 to Leon et al. (1982)
4,352,881 to Inagawa et al. (1982)
4,357,420 to Bostick et al. (1982)
4,368,261 to Klase et al. (1983)
4,371,611 to Fusee et al. (1983)
4,394,445 to Nix et al. (1983)
4,415,655 to de Castro et al. (1983)
4,438,124 to Meister et al. (1984)
4,445,594 to Buckmann (1984)

4,485,177 to Siedel et al. (1984)

The above patents also include additional information and details about methods for detecting AMP, ADP or ATP, discussed above, and especially about methods involving pyruvate kinase and lactate dehydrogenase.

Additionally, the ADP produced in the digestion step may be determined directly by chromatography such as HPLC or fast protein liquid chromatography (using Pharmacia's FPLC instrument). See G.A. Orr et al., *Analytical Biochem.*, vol. 142, pp. 232-234 (1984).

Depending upon which ATP-detecting scheme is used, it may be desirable to perform the third (detecting step) only after the first two steps are completed. This would enable ATP to be accumulated, e.g., in an incubation vessel, and then detected within a consolidated time period, e.g., in a luminometer chamber. In other cases, it may be desired that reagents for all three steps be present together. One may mix the sample (with endogenous AMP, ADP and ATP removed or compensated for) with PNP, creatine phosphate, CPK, myokinase, luciferin and luciferase. One may also mix the sample (with endogenous ADP and ATP removed or compensated for) with PNP, phosphoenol pyruvate (PEP), NADH, lactate dehydrogenase (LDH) and fructose-6-phosphate. See U.S. Pat. No. 4,446,231, Example 1, Table 1 for an analogous assay for ADP. In this latter instance, the ADP generated by PNP is phosphorylated to ATP, but the ATP is not detected. Instead, PEP is concurrently converted to pyruvate, and the pyruvate reduces NADH to NAD (catalyzed by LDH). The disappearance of NADH is monitored by absorbance at 340 nm or by fluorimetric measurement.

The use of subtraction in the present method can be illustrated by the following five cases, each of which can be performed on equal aliquots of a sample:

TABLE 1

| Case | Reagents | Measures |
|---|---|---|
| 1 | Lin/Lase | ATP |
| 2 | PEP/PK Lin/Lase | ADP, ATP |
| 3 | GTP/MK PEP/PK | AMP, ADP, ATP |
| 4 | Pi/PNP PEP/PK Lin/Lase | ADP, ATP, mRNA |
| 5 | PDE GTP/MK PEP/PK Lin/Lase | AMP, ADP, ATP, RNA |

Lin = D-luciferin
Lase = Luciferase
PEP = Phosphoenolpyruvate
PK = Pyruvate Kinase
GTP = Guanidine Triphosphate
MK = Myokinase
Pi = Inorganic Phosphate
PNP = Polynucleotide Phosphorylase
PDE = Phosphodiesterase
ATP = Adenosine Triphosphate
ADP = Adenosine Diphosphate
AMP = Adenosine Monophosphate
mRNA = Messenger Ribonucleic Acid (or similar RNA or RNA/DNA with adenosine - containing digestable ribonucleotide segment)

Making all five measurements enables any of a variety of values to be determined, e.g.:

$$[mRNA] = Value_4 - Value_2$$

or $$[RNA] = Value_5 - Value_3$$

The two quantities should differ somewhat because the AMP-generating digestion enzyme (e.g., PDE or snake venom phosphodiesterase) is likely to digest single-stranded ribonucleotide segments other than 3'-terminal ribonucleotide segments, while the ADP-generating digestion enzyme (e.g., PNP or *M. leuteus* polynucleotide phosphorylase) is, under defined reaction conditions, specific for 3'-terminal ribonucleotide segments.

EXAMPLE 1

Bioluminescent Detection of ribo(Ap)$_9$A

Standard dilution series were prepared for commercially obtained (Ap)$_9$A (P.L. Biochemicals) and *E. coli* 5S ribosomal RNA 95S rRNA, Boehringer-Mannheim). These dilutions were based on molar extinction values of 14500 (259 nm) and $1.2 \times 10^6$ (260 nm) for (Ap)$_9$A and 5 SrRNA respectively. RNAs were converted to nucleoside triphosphates prior to bioluminescent detection of ATP as follows: To each 20 μl sample of a particular dilution of an RNA was added an equal volume of a phosphorysis/kinase reagent mixture to give a final concentration of: 20 mM inor phosphate, 5 mM MgCl$_2$, 50 mM Tris-HCl (pH 8.5), 1 mM 2-mercaptoethanol, 175 units/ml polynucleotide phosphorylase, 0.8 mg/ml phosphoenol pyruvate; and 0.2 units/ml pyruvate kinase. Following incubation for 30 minutes at either 36° C. or 50° C. as indicated below, the samples were adjusted to a final volume of 250 ul and the adenosine triphosphate quantitated using a standard bioluminescence assay (LKB). Following a delay period of 180 seconds bioluminescence was measured in the integrating mode for a period of 60 seconds.

Table 2 shows the results of analysis of ribo(Ap)$_9$A at different levels.

BIOLUMINESCENT DETECTION OF RNA USING POLYNUCLEOTIDE PHOSPHORYLASE AND PYRUVATE KINASE

TABLE 2

| | Detection of (Ap)$_9$A | |
|---|---|---|
| Sample | moles (Ap)$_9$A | mV |
| 1 | 0 (minus RNA) | 8911 |
| 2 | $5 \times 10^{-15}$ | 78050 |
| 3 | $2.5 \times 10^{-15}$ | 43560 |
| 4 | $5 \times 10^{-16}$ | 13750 |
| 5 | $2.5 \times 10^{-16}$ | 9808 |
| 6 | $5 \times 10^{-15}$ (-PNPase) | 6708 |

TABLE 3

| Sample | Oligo dG Cellulose Fraction | Pmol Competitor | Pmol Probe DNA[1] | cpm | % Total cpm | Bioluminescence (mv) |
|---|---|---|---|---|---|---|
| 1 | 0.2 M NaCl | 0 | 1.0 | 35 | 1.3 | 310 |
| | H$_2$O | | | 2662 | | 40138 |
| | Total | | | 2698 | | — |
| 2 | 0.2 M | 0.1 | 1.0 | 286 | 9.4 | 2914 |
| | H$_2$O | | | 2763 | | 33820 |
| | Total | | | 3050 | | — |

TABLE 3-continued

| Sample | Oligo dG Cellulose Fraction | Pmol Competitor | Pmol Probe DNA[1] | cpm | % Total cpm | Bioluminescence (mv) |
|---|---|---|---|---|---|---|
| 3 | 0.2 M | 0.2 | 1.0 | 599 | 21.3 | 6214 |
|   | H$_2$O |   |   | 2215 |   | 31640 |
|   | Total |   |   | 2815 | — |   |
| 4 | 0.2 M | 0.5 | 1.0 | 1167 | 42.3 | 12913 |
|   | H$_2$O |   |   | 1591 |   | 18495 |
|   | Total |   |   | 2758 | — |   |
| 5 | 0.2 M | 1.0 | 1.0 | 2724 | 89.0 | 26590 |
|   | H$_2$O |   |   | 337 |   | 465 |
|   | Total |   |   | 3061 | — |   |
| 6 | 0.2 M | 1.0 | 1.0 | 2720 | 91.4 | 27613 |
|   | H$_2$O |   |   | 269 |   | 603 |
|   | Total |   |   | 2989 | — |   |
|   |   |   |   | Bkg = 25 cpm | 0.2 M NaCl - RNA | Bkg = 4613 |
|   |   |   |   |   | H$_2$O - RNA | 5048 |

[1]Approximately 0.2 pmoles PM27rAn per pmole probe DNA annealed during hybrid formation.

EXAMPLE 2

This Example illustrates differences between three RNAs digested by PNP at 37° C. or 50° C. The RNAs were:

(1) 1 pmol of ribo (Ap)$_9$A as in Example 1;
(2) 1 pmol of E. coli 5S rRNA; and
(3) RNA resulting from the transcription with P32 labeled ATP of pSp64 plasmid DNA which had been linearized with EcoRI restriction enzyme (a 52-mer RNA oligomer with limited double-stranded regions).

Each RNA was reacted with PNP at 37° C. and separately at 50° C. Both sets of samples 1 and 2 were phosphorylated and detected by bioluminescence as in Example 1. Comparing, for each sample, the mV values at 37° C. and 50° C. digestion temperature, the decamer (sample 1) gave a value for the 37° C. digestion which was 98% of the value for the 50° C. digestion. The ribosomal RNA (sample 2) gave a bioluminescence value for the 37° C. digestion which was 35% of the value for the 50° C. digestion. Sample 3 is expected to give an intermediate ratio of bioluminescence. The results of analyses of sample 3 (for the 37° C. or 50° C. digestion) by polyethyleneimine cellulose chromatography in 0.8 M LiCl, 0.8 M HAc followed by excision counting of the radioactivity at locations corresponding to ATP and unphosphorylized RNA was:

|     | 37° C. | 50° C. |
|---|---|---|
| ATP | 53% | 98% |
| RNA | 47% | 2% |

These data show the controllability of which ribonucleotide segments of a sample are digested by PNP through reaction temperature.

EXAMPLE 3

Applicants hereby incorporate by reference Example 2 of U.S.S.N. 729,503. Table 3 summarizes the results of such experiment.

EXAMPLE 4

The following shows the lack of effect of DNA upon the present RNA-detecting method.

Calf thymus DNA was treated with base (1N KOH 80° C. for 2 hrs.) to remove endogenous RNA, neutralized with acetic acid and precipitated with ethanol. 1, 3 and 5 pmoles of 5S rRNA were phosphorylized for 60 minutes at 50° C. and the ADP converted to ATP as in Examples 1 and 2 in the absence or presence of 3 ug (150 ug/ml) calf thymus DNA. ATP was measured by bioluminescence as described above. The results were:

| 5S RNA (pmol) | DNA (ug) | Bioluminescence (mV) |
|---|---|---|
| 0 | 0 | 8,850 |
| 0 | 3 | 8,930 |
| 1 | 0 | 89,867 |
| 1 | 3 | 91,320 |
| 3 | 0 | 279,568 |
| 3 | 3 | 289,576 |
| 5 | 0 | 456,080 |
| 5 | 3 | 449,898 |

EXAMPLE 5

The following Example illustrates digestion of poly A to AMP, phosphorylation to ATP and detection by bioluminescence. Such techniques can be used in the present method.

To 10 ul of a solution of unpurified poly(riboadenosine phosphate) (poly A) (from Boehringer-Mannheim, molecular weight 1.5 million) was added 1.0 unit of snake venom phosphodiesterase (PDE) (Worthington). Controls were prepared without PDE. Concentrations of poly A varied from 0.001 to 1.0 mg/ml such that the samples had 0.01, 0.1, 1.0 and 10 micrograms of poly A each. The reaction volume was increased to 25 ul with 50 mM Tris (pH 8.5), 5.0 mM potassium phosphate, 1.0 mM MgCl$_2$. The mixture was incubated first at 37° C. for 10 minutes, then at approximately 100° C. for 2 minutes to inactivate the enzyme. To this was added 20 ul of a solution containing 100 mM Tris(pH 7.75), 2.0 mM EDTA, 125 mM MgSO$_4$, 313 mM K$_2$SO$_4$, 26.8 mM phosphoenolpyruvate, 2 units pyruvate kinase, and 40 units myokinase (both enzymes from rabbit muscle and purchased from Sigma). The reaction volume was increased to 500 ul with 50 mM Tris (pH 7.75) and the solution incubated for 10 minutes at 37° C. The amount of ATP produced was determined using the LKB bioluminescence assay (firefly luciferase assay) on 500 ul of each sample or control and 50 ul of strandard luciferin/-luciferase reagent. Digestion to AMP and subsequent conversion to ATP was observed, as indicated by the following Table. In these runs, CTP was present at the 25 μmol in the 20 ul solution added after digestion. No effect was seen comparing these with other runs in which no CTP was added. This suggest that sufficient nucleoside triphosphates (NTP) were present as impurities in various reagents to support or initiate the myokinase reaction.

| Poly(rA) (MW 1,500,000) (micrograms) | W/O PDE | With PDE |
|---|---|---|
| 0.01 | 515 | 722 |
| 0.1 | 1650 | 14,640 |
| 10 | 22,540 | 100,000 |

The tubes prepared from 10 ul of 0.001 mg/ml poly A (and thus 0.01 ug of poly A) gave substantially the same bioluminescence values with and without the phosphodiesterase.

What is claimed is:

1. A method for the determination of polynucleotides having 3'-terminal polyriboadenosine segments in a sample which comprises the steps:
   (a) digesting the nucleic acid of a sample with a polynucleotide phosphorylase in the presence of inorganic phosphate to convert 3'-terminal polyriboadenosine segments to adenosine diphosphate (ADP);
   (b) phosphorylating the ADP produced in the digesting step (a) to produce ATP; and
   (c) detecting either the ATP produced in the phosphorylating step (b) or a by-product of the phosphorylating step.

2. The method of claim 1 wherein the polynucleotides having 3'-terminal polyriboadenosine segments are eukaryotic mRNA.

3. The method of claim 1 wherein the polynucleotides having a 3'-terminal polyriboadenosine segment are reagents whose presence in the reaction mixture for the digesting step (a) is a function of a specific binding reaction.

4. The method of claim 3 wherein the polynucleotides having a 3'-terminal polyriboadenosine segment contain a target binding region substantially complementary to a selected target nucleotide sequence.

5. The method of claim 4 wherein the target binding region is DNA.

6. The method of claim 1 wherein the phosphorylating step (b) is conducted with a kinase and an organophosphate co-reactant.

7. The method of claim 6 wherein the kinase and organophosphate co-reactant of the phosphorylating step (b) are present during the digesting step (a), whereby the forward reaction of the digesting step (a) is enhanced.

8. The method of claim 7 where the kinase is selected from the group consisting of creatine kinase and pyruvate kinase.

9. The method of claim 7 wherein the detecting step (c) comprises reacting the ATP produced in the phosphorylating step (b) with luciferin in the presence of a luciferase.

10. The method of claim 7 wherein the detecting step (c) comprising reacting the byproduct from the phosphorylating step (b) in an oxidation reaction.

11. The method of claim 1 wherein the detecting step (c) comprises reacting the ATP produced in the phosphorylating step (b) with luciferin in the presence of a luciferase.

12. A kit for the determination of polynucleotides having 3'-terminal polyriboadenosine segments which comprises:
    (a) polynucleotide phosphorylase,
    (b) a kinase capable of converting ADP to ATP and its organophosphate co-reactant, and
    (c) reactants for the detection of ATP.

13. The kit of claim 12 wherein the reactants (c) comprises a luciferase and luciferin.

14. The kit of claim 12 wherein the polynucleotide phosphorylase, kinase and organophosphate co-reactant are packaged together.

15. The kit of claim 12 wherein the polynucleotide phosphorylase is derived from E. coli or M. leuteus.

16. A method for the determination of polynucleotides having single-stranded ribonucleotide segments which comprises the steps:
    (a) digesting the nucleic acid of a sample with a phosphodiesterase which is a ribonuclease to convert single-stranded ribonucleotide segments to ribonucleotide monophosphates including AMP;
    (b) phosphorylating the AMP produced in the digesting step (a) to ADP;
    (c) further phosphorylating the ADP produced in the phosphorylating step (c) to ATP; and
    (d) detecting either the ATP produced in the further phosphorylating step (c) or a by-product of the further phosphorylating step (c).

17. The method of claim 16 wherein the digesting step (a) is conducted with a phosphodiesterase.

18. The method of claim 16 wherein the phosphorylating step (b) is conducted with myokinase and a nucleoside triphosphate other than ATP.

19. The method of claim 18 wherein the further phosphorylating step (c) is conducted with a kinase and an organophosphate co-reactant for the kinase.

20. The method of claim 19 wherein the kinase and organophosphate co-reactant are present during the phosphorylating step (b), whereby ADP is further phosphorylated to ATP as it is formed.

21. A kit for the determination of polynucleotides having single-stranded ribonucleotide segments comprising reagents and enzymes effective to:
    (a) digest the single-stranded ribonucleotide segments to ribonucleoside monophosphates including AMP;
    (b) phosphorylate AMP to ADP;
    (c) further phosphorylate ADP to ATP; and
    (d) detect either ATP or a byproduct of the further phosphorylation reaction.

22. The kit of claim 21 comprising:
    (a) a phosphodiesterase,
    (b) myokinase and a nucleoside triphosphate other than ATP,
    (c) a kinase capable of phosphorylating ADP to ATP and an organophosphate co-reactant for the kinase, and
    (d) an enzyme producing detectable light from ATP and a co-reactant for the enzyme.

23. The kit of claim 22 wherein the kinase is pyruvate kinase or creatine kinase.

24. The kit of claim 23 wherein the myokinase, nucleoside triphosphate, kinase and organphosphate co-reactant are packaged together.

25. The kit of claim 23 wherein the enzyme is luciferase and its co-reactant is luciferin.

* * * * *